US012611227B2

(12) United States Patent
Higdon

(10) Patent No.: US 12,611,227 B2
(45) Date of Patent: Apr. 28, 2026

(54) MEDICAL DEVICE DELIVERY APPARATUS AND METHOD

(71) Applicant: Vanderbilt University, Nashville, TN (US)

(72) Inventor: Kent K. Higdon, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 741 days.

(21) Appl. No.: 18/000,502

(22) PCT Filed: May 28, 2021

(86) PCT No.: PCT/US2021/035012
§ 371 (c)(1),
(2) Date: Dec. 1, 2022

(87) PCT Pub. No.: WO2021/247444
PCT Pub. Date: Dec. 9, 2021

(65) Prior Publication Data
US 2023/0255663 A1 Aug. 17, 2023

Related U.S. Application Data

(60) Provisional application No. 63/032,814, filed on Jun. 1, 2020.

(51) Int. Cl.
*A61F 2/12* (2006.01)
*A61B 17/34* (2006.01)
*A61B 90/00* (2016.01)

(52) U.S. Cl.
CPC .......... *A61B 17/3468* (2013.01); *A61B 90/02* (2016.02)

(58) Field of Classification Search
CPC .................. A61B 17/3468; A61B 90/02; A61F 2220/0075; A61F 2230/0067; A61F 2250/0003; A61F 2250/0018; A61F 2/12
See application file for complete search history.

(56) References Cited

U.S. PATENT DOCUMENTS 5,723,006 A * 3/1998 Ledergerber .............. A61F 2/12
600/233
8,206,443 B2 6/2012 Preissman
(Continued)

FOREIGN PATENT DOCUMENTS

GB 1340693 A 12/1973
WO 2018162345 A1 9/2018

OTHER PUBLICATIONS

International Search Report mailed Sep. 29, 2021 for corresponding International Application No. PCT/US21/35012.

*Primary Examiner* — Suzette J Gherbi
(74) *Attorney, Agent, or Firm* — Tarolli, Sundheim, Covell & Tummino LLP

(57) ABSTRACT

A delivery device configured to deliver a medical device into a patient is provided. The delivery device includes a distal ring and a transition tunnel. The transition tunnel is sized to receive a medical device. The transition tunnel is coupled to the distal ring. The delivery device also includes a proximal chute that has an inner perimeter and an outer perimeter. The inner perimeter of the proximal chute is coupled to the transition tunnel. The proximal chute is configured to transition between opened and closed conditions. The outer perimeter of the proximal chute in the opened condition is spread radially outward from the transition tunnel and defines an opening for receiving the medical device. The proximal chute in the closed condition is configured to at least partially prevent the medical device from egressing the delivery device.

18 Claims, 5 Drawing Sheets

(56)  References Cited

U.S. PATENT DOCUMENTS

| | | | | |
|---|---|---|---|---|
| 10,105,213 | B2 * | 10/2018 | Weinzweig | ............ A61B 90/08 |
| 10,722,335 | B1 * | 7/2020 | Rosenberg | ................ A61F 2/12 |
| 11,083,564 | B2 * | 8/2021 | Gryskiewicz | ............. A61F 2/12 |
| 11,672,565 | B2 * | 6/2023 | Viquez | ............... A61B 17/3468 |
| | | | | 623/8 |
| 11,786,360 | B2 * | 10/2023 | Graf | .......................... A61F 2/12 |
| | | | | 623/8 |
| 11,903,814 | B2 * | 2/2024 | Graf | .......................... A61F 2/12 |
| 12,102,309 | B2 * | 10/2024 | Lee | ................. A61B 17/12172 |
| 12,318,276 | B2 * | 6/2025 | Bakshandeh | ......... A61F 2/0095 |
| 2007/0038310 | A1 * | 2/2007 | Guetty | ..................... A61F 2/12 |
| | | | | 623/23.72 |
| 2009/0048569 | A1 | 2/2009 | Salehi | |
| 2010/0280610 | A1 * | 11/2010 | Preissman | ................. C09J 5/00 |
| | | | | 623/8 |
| 2011/0092778 | A1 | 4/2011 | Butler | |
| 2015/0374478 | A1 | 12/2015 | Anderson | |
| 2016/0243333 | A1 * | 8/2016 | Seward | .................. A61L 29/14 |
| 2017/0312111 | A1 * | 11/2017 | Sharma | ................... A61F 5/003 |
| 2019/0274819 | A1 * | 9/2019 | Graf | .......................... A61F 2/12 |
| 2022/0000604 | A1 * | 1/2022 | Graf | ............... A61B 17/00234 |
| 2023/0355391 | A1 * | 11/2023 | Basude | .................. A61F 2/246 |

* cited by examiner

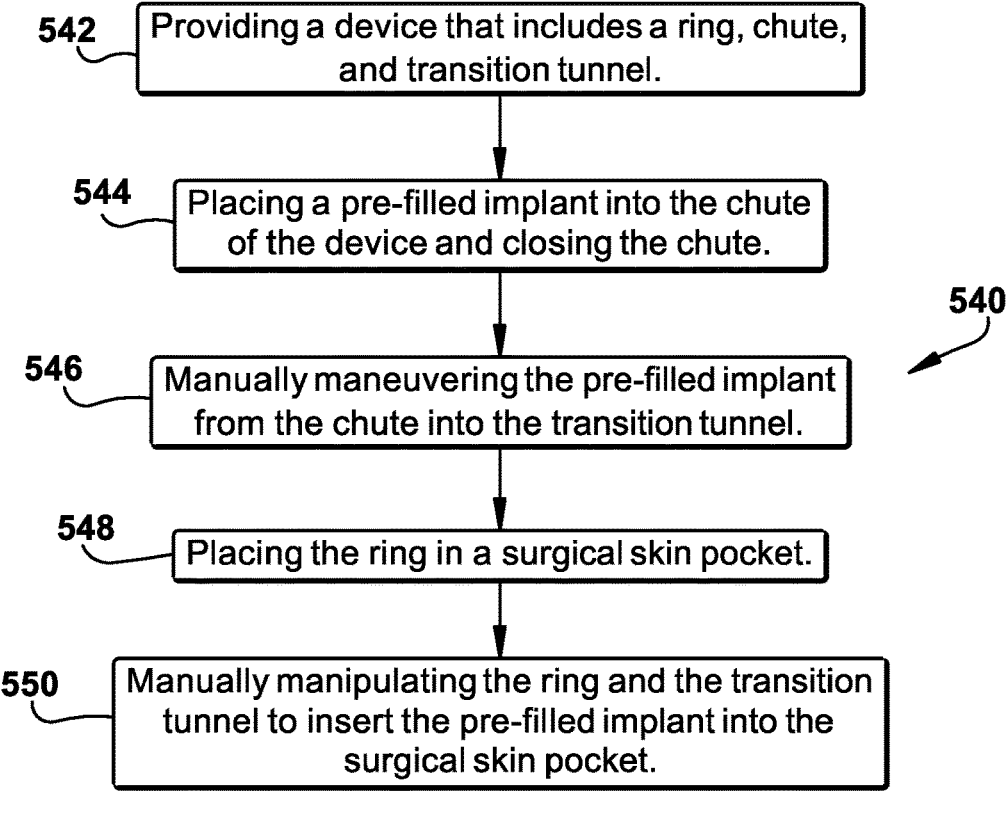

542 — Providing a device that includes a ring, chute, and transition tunnel.

544 — Placing a pre-filled implant into the chute of the device and closing the chute.

540

546 — Manually maneuvering the pre-filled implant from the chute into the transition tunnel.

548 — Placing the ring in a surgical skin pocket.

550 — Manually manipulating the ring and the transition tunnel to insert the pre-filled implant into the surgical skin pocket.

Fig. 5

654 — Providing a device that includes a ring, chute, and transition tunnel.

656 — Placing the ring in a surgical skin pocket.

652

658 — Spreading the chute out so the chute covers the skin directly surrounding the surgical skin pocket.

660 — Placing an unfilled prosthesis in the surgical skin pocket.

662 — Filling the unfilled prosthesis.

Fig. 6

MEDICAL DEVICE DELIVERY APPARATUS AND METHOD

CROSS-REFERENCE TO RELATED APPLICATIONS

This application is a U.S National Stage application under 35 USC 371 of PCT Application Serial No. PCT/US2021/035012. filed May 28, 2021 which claims priority from U.S. Provisional Application No. 63/032,814, filed 1 Jun. 2020, the subject matter of both which is incorporated herein by reference in its entirety.

RELATED APPLICATION

This application claims priority from U.S. Provisional Application No. 63/032,814, filed 1 Jun. 2020, the subject matter of which is incorporated herein by reference in its entirety.

TECHNICAL FIELD

The present disclosure relates to an apparatus and methods or processes for delivering a medical device to the body of the subject. More particularly, the present disclosure relates to a device for inserting a prosthesis into a surgical skin pocket of a subject.

BACKGROUND

Breast implants are a manufactured medical prosthesis designed to augment, reconstruct or create the physical form of a breast. Patients undergo breast augmentation surgery for a number of reasons including cosmetic reasons as well as for reconstructive purposes following a mastectomy for breast cancer. There are two basic types of breast implants, saline and silicone gel implants. An empty saline implant can be delivered to the patient through a small incision and then filled once it is placed in the body. However, silicone gel implants come pre-filled. Thus, larger incisions are generally required to place silicone gel implants compared with saline implants. Larger incisions may increase the patient's risk for wound healing complications. The typical process for inserting a silicone gel implant involves hand manipulation. Hand manipulation can be time consuming and can increase the difficulty of the procedure compared to a fill-in-place implant.

Thus, a device and a process for delivering a breast implant to the body of a patient that reduces delivery challenges may be desirable.

SUMMARY

In an aspect, a delivery device configured to deliver a medical device into a patient is provided. The delivery device comprises a distal ring and a transition tunnel. The transition tunnel is sized to receive a medical device. The transition tunnel is coupled to the distal ring. The delivery device also comprises a proximal chute including an inner perimeter and an outer perimeter. The inner perimeter of the proximal chute is coupled to the transition tunnel. The proximal chute is configured to transition between opened and closed conditions. The outer perimeter of the proximal chute in the opened condition is spread radially outward from the transition tunnel and defines an opening for receiving the medical device. The proximal chute in the closed condition is configured to at least partially prevent the medical device from egressing the delivery device.

In an aspect, alone or in combination with any other aspect, a process for inserting a pre-filled implant into a surgical skin pocket of a subject is provided. The process comprises providing the delivery device. The proximal chute is transitioned into the opened condition. The pre-filled implant is placed into the proximal chute of the delivery device through the opening. With the pre-filled implant in the proximal chute, the proximal chute is transitioned to the closed condition. The pre-filled implant is maneuvered from the proximal chute into the transition tunnel. The distal ring is placed in the surgical skin pocket. The distal ring and the transition tunnel are manipulated to insert the pre-filled implant into the surgical skin pocket.

In an aspect, alone or in combination with any other aspect, a process for delivering a prosthesis into a surgical skin pocket of a subject is provided. The process comprises providing the delivery device. The distal ring is placed in the surgical skin pocket. The proximal chute is spread out into the opened condition so that the proximal chute covers the skin directly surrounding the surgical skin pocket. An unfilled prosthesis is placed into the surgical skin pocket. The prosthesis is filled.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 5 is a flowchart at least partially describing a process of inserting a pre-filled implant into a surgical skin pocket of a subject in accordance with an aspect of the present disclosure; and FIG. 6 is a flowchart at least partially describing a process for delivering a prosthesis into a surgical skin pocket of a subject in accordance with an aspect of the present disclosure.

DESCRIPTION OF EMBODIMENTS

Figure 1:
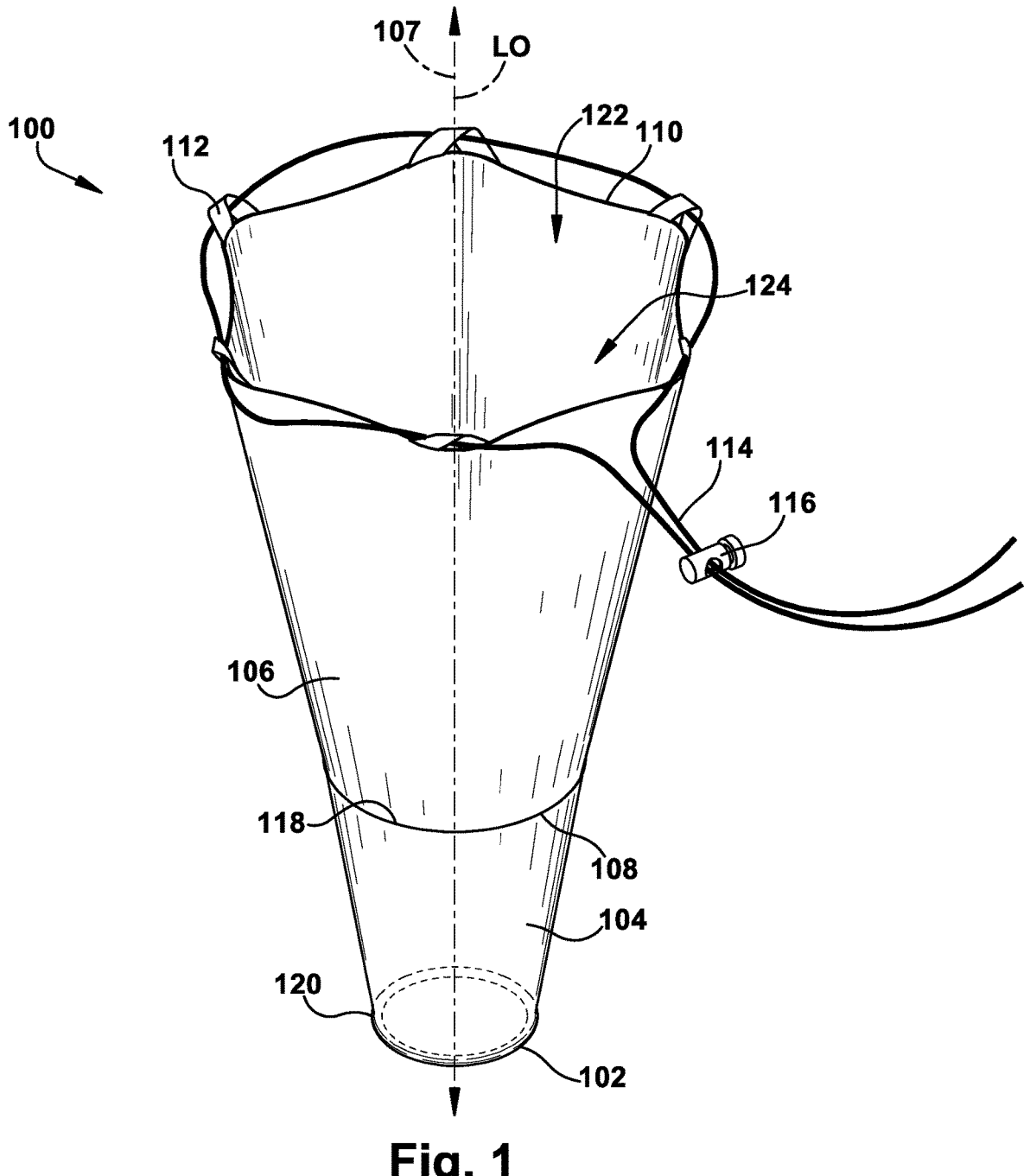
FIG. 1 is a perspective view showing an example device for delivering a prosthesis to a surgical pocket in accordance with an aspect of the present disclosure, including the device in a first condition.

Unless defined otherwise, all technical and scientific terms used herein have the same meaning as is commonly understood by one of ordinary skill in the art to which the present disclosure pertains.

As used herein, the term "patient" can refer to any warm-blooded organism including, but not limited to, human beings, pigs, rats, mice, dogs, goats, sheep, horses, monkeys, apes, rabbits, cattle, farm animals, livestock, etc.

Additionally, the terms "subject" and "patient" are used herein interchangeably and are synonymous.

As used herein, the term "user" can be used interchangeably to refer to an individual who prepares for, assists with, and/or performs a procedure. Additionally, the terms "user" and "physician" can be used herein interchangeably.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" can be interpreted to include X and Y.

As used herein, the phrase "at least one of X and Y" can be interpreted to include X, Y, or a combination of X and Y. For example, if an element is described as having at least one of X and Y, the element may, at a particular time, include X, Y, or a combination of X and Y, the selection of which could vary from time to time. In contrast, the phrase "at least one of X" can be interpreted to include one or more Xs.

It will be understood that when an element is referred to as being "on," "attached" to, "connected" to, "coupled" with, "contacting," etc., another element, it can be directly on, attached to, connected to, coupled with or contacting the other element or intervening elements may also be present.

It will be understood that the spatially relative terms can encompass different orientations of a device in use or operation, in addition to the orientation depicted in the Figures. For example, if a device in the Figures is inverted, elements described as "under" or "beneath" other elements or features would then be oriented "over" the other elements or features.

As used herein, when terms "distal" and "proximal" are used to refer to a portion of the device, they refer to the device in its delivery configuration. The term "proximal" can refer to close to the operator (less into the body) and "distal" can refer to remote from the operator (further into the body).

The invention comprises, consists of, or consists essentially of the following features, in any combination.

The present disclosure describes a device configured to deliver a medical device, such as a prosthesis, to a surgical pocket. In one aspect the prosthesis is a breast prosthesis. The breast prosthesis can be a pre-filled breast implant or an unfilled breast implant. The design of the disclosed device allows for both saline and silicone implants to be delivered to a surgical pocket in a manner that helps prevent the implant from touching the patient's skin. Additionally, the design of the disclosed device allows for desirably evenly distributed forces to be applied to the implant when inserting the implant into the surgical pocket.

Figure 2:
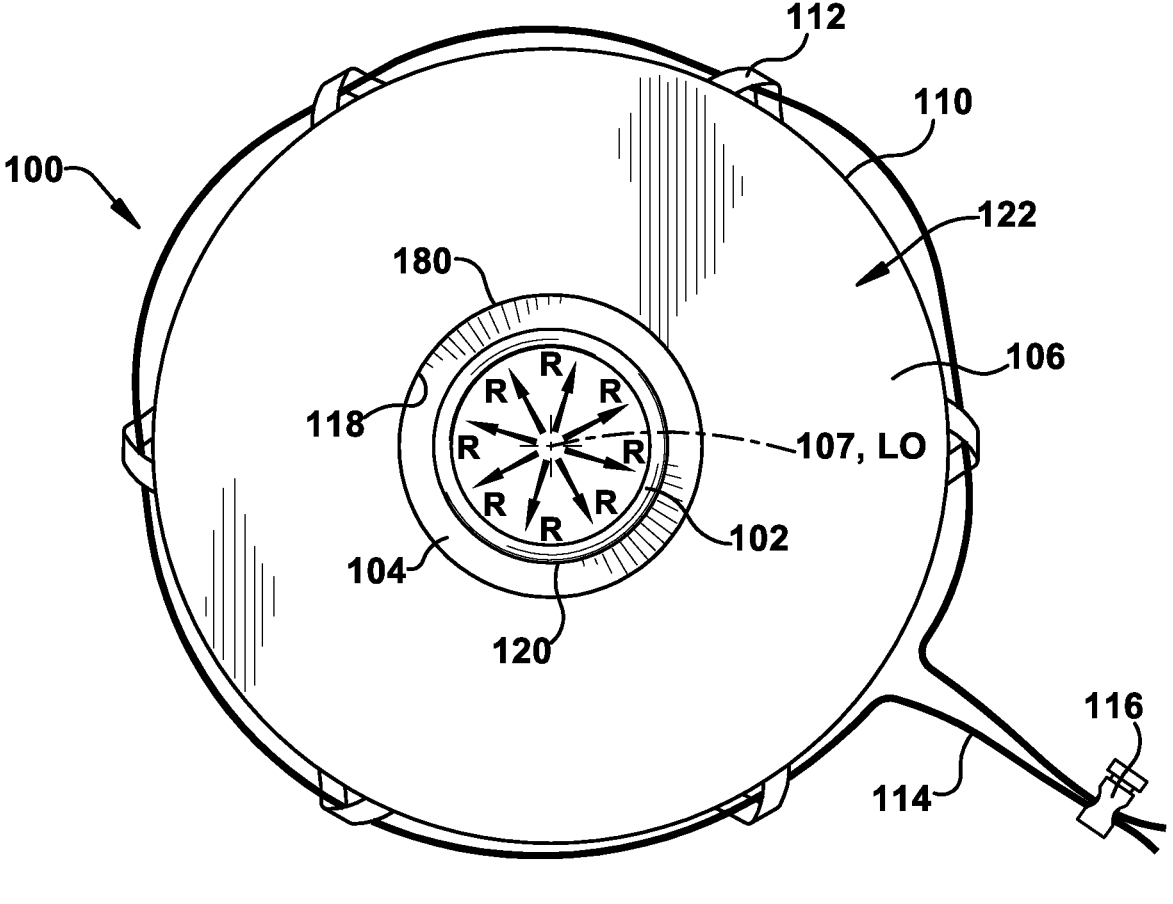
FIG. 2 is a plan view showing an example device for delivering a prosthesis to a surgical pocket in accordance with an aspect of the present disclosure, including the device in a second condition.

FIGS. 1-2 illustrate a delivery device 100 for use delivering a medical device, such as a prosthesis, to a surgical pocket, described herein as being a surgical skin pocket. It is contemplated, though, that any artificial or natural aperture leading toward an interior of a patient's body could be a suitable reception site for a prosthesis installed with assistance from the apparatus and/or method of the present invention. As shown in FIG. 1, the device 100 can include a flexible distal ring 102, a transition tunnel 104, and a proximal chute 106 that extend along a central longitudinal axis 107. The term "longitudinal" is used herein to indicate a substantially vertical direction, in the orientation of FIG. 1, and is indicated at "LO" in FIG. 1. The flexible distal ring 102, the transition tunnel 104, and the proximal chute 106 can be separately formed pieces that are joined together to form the device 100. The proximal chute 106 can have an inner perimeter 108 and an outer perimeter 110.

The transition tunnel 104 can be coupled to the distal ring 102 and the inner perimeter 108 of the proximal chute 106. In certain instances, the transition tunnel 104 can be coupled to the distal ring 102 and to the proximal chute 106 by being bonded, sealed, sewn, adhered, by any other suitable direct or indirect attachment or coupling means, or by any combination thereof. In certain instances, the transition tunnel 104 can have a truncated cone shape such that a proximal end 118 of the transition tunnel has a larger diameter than a distal end 120 of the transition tunnel. In other instances the transition tunnel 104 can have a cylindrical shape. The transition tunnel 104 can be sized to hold a variety of prostheses, singly or in combination, or sized to hold a selected prosthesis of a predetermined size.

In one instance, the proximal chute 106 can be configured so that it can transition between an opened and a closed condition. When the proximal chute 106 is in an opened condition, the proximal chute 106 is configured so that the outer perimeter 110 of the proximal chute 106 defines an opening 122 sized to receive a prosthesis. FIG. 2 depicts the proximal chute 106 in the opened condition. In FIG. 2, the outer perimeter 110 of the proximal chute 106 is spread radially outward from the transition tunnel 104 and has a diameter that defines an opening 122 for receiving the prosthesis. The term "radial" is used herein to indicate a direction substantially perpendicular to the "longitudinal" direction, and is shown via arrows R in FIG. 2 emanating from the central longitudinal axis 107, in the orientation of FIG. 2. The proximal chute 106 can be substantially flat and spread into a substantially circular shape when in the opened condition. Although the proximal chute 106 has been described and shown as having a substantially circular shape in the opened condition, the opened proximal chute 106 can instead be shaped as a hexagon, a square, a rectangle, a square, any desired polygon, any desired rounded shape, or any combination thereof.

Figure 3:
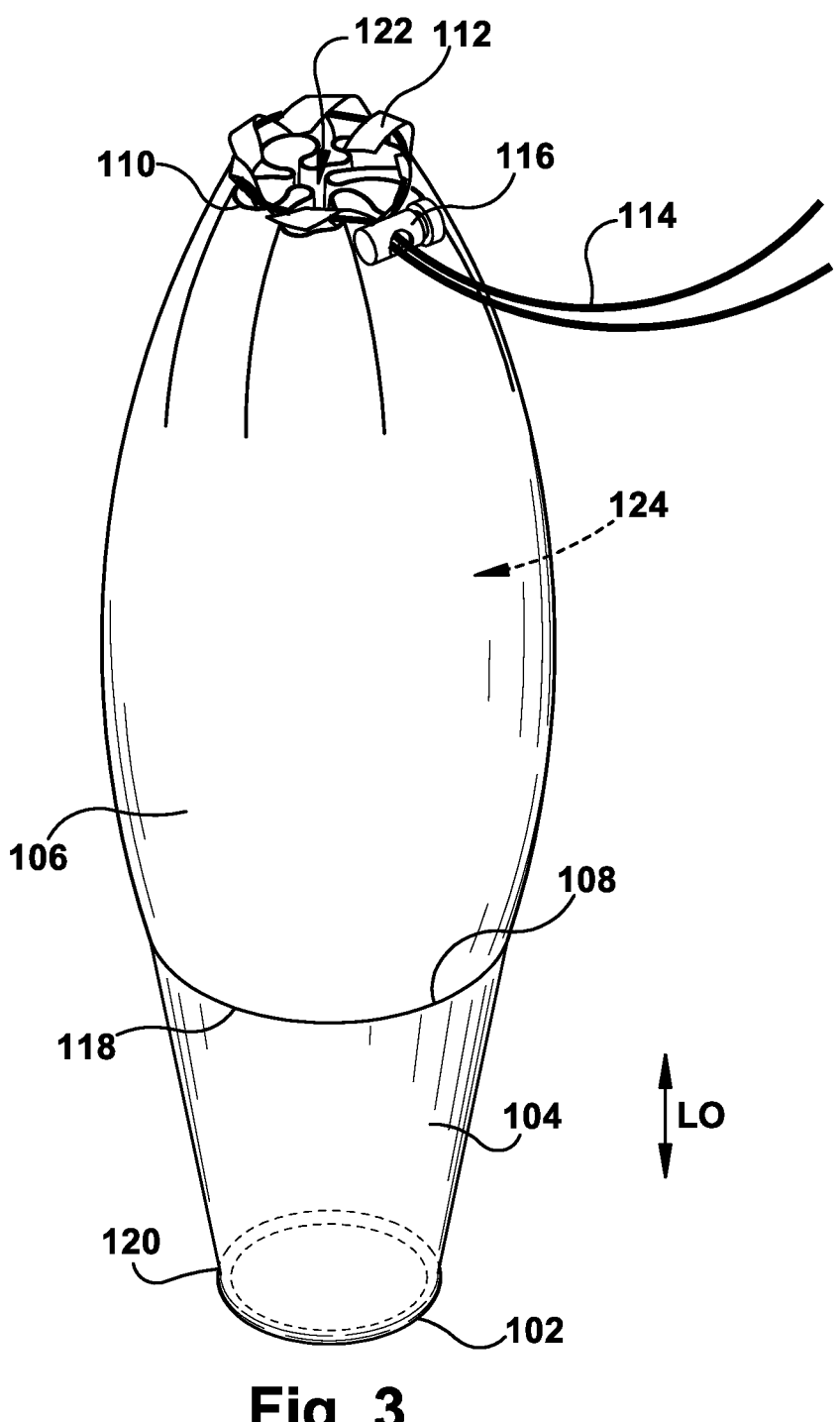
FIG. 3 is a perspective view showing an example device for delivering a prosthesis to a surgical pocket in accordance with an aspect of the present disclosure, including the device in a third condition.

When the proximal chute 106 is in the closed condition, the opening 122 defined by the outer perimeter 110 of the proximal chute 106 is configured so that it can be closed to capture a prosthesis. By closed it is meant that the opening 122 is reduced to a degree at which a prosthesis received in the proximal chute 106 or the device 100 is partially and/or substantially prevented from egressing from the device 100 through the opening 122. As shown in FIGS. 1 and 3, the closed proximal chute 106 can define a chamber 124 extending between the proximal end 118 of the transition tunnel 104 and a portion of the proximal chute 106, such as, for example, the outer perimeter 110 of the proximal chute 106, for capturing the prosthesis. The chamber 124 can be sized to hold a variety of prostheses, singly or in combination, or sized to hold a selected prosthesis of a predetermined size.

FIG. 1 depicts the proximal chute in an example configuration with the proximal chute 106 in the closed condition, which can alternatively be referred to as a partially closed condition. In the partially closed condition, the outer perimeter 110 of the proximal chute 106 can be spread longitudinally outward from the transition tunnel 104 and the opening 122 can be reduced from that of the opening 122 in the opened condition. The opening 122 in FIG. 1, however, may be partially closed so that a prosthesis can be partially prevented from egressing from the device 100 through the opening 122. As shown in the example configuration of FIG. 1, the device 100 can have a truncated cone shape when the proximal chute 106 is in the partially closed condition.

FIG. 3 depicts another example configuration of the proximal chute 106 in the closed condition. In FIG. 3, the outer perimeter 110 of the proximal chute 106 is spread longitudinally outward from the transition tunnel 104 and the opening 122 is reduced from that of the opening 122 in the partially closed condition. For example, the opening 122 in the configuration of FIG. 3 can be completely or substantially closed so that a prosthesis can be completely or substantially prevented from egressing from the device 100 through the opening 122.

One skilled in the art could envision a variety of ways in which the proximal chute 106 can be configured so that it can be closed to capture a prosthesis. For example, as seen in FIGS. 1-3, a series of flexible loops 112 can surround the outer perimeter 110 of the proximal chute 106. A cord 114 can run through one or more of the flexible loops 112. In the opened condition, as shown in FIG. 2, the diameter of the outer perimeter 110 of the proximal chute 106 is configured to reduce or constrict in response to tension forces applied to the cord 114. As described below, the cord 114 acts as a drawstring for selectively closing the proximal chute 106.

Configured as described above, the cord 114 cooperates with the loops 112 to serve as a drawstring that closes the opening 122 of the proximal chute 106 when the cord 114 is tensioned. When the cord 114 is tensioned, the size or circumference of the portion of the cord 114 extending through the loops 112 is reduced, which, because the cord 114 extends through the loops 112, reduces the diameter of the outer perimeter 110 and constricts or otherwise draws closed the opening 122 defined by the outer perimeter 110 of the proximal chute 106.

The tension applied to the cord 110 may thus maintain the proximal chute 106 closed. In certain instances, a locking device 116 can be used to secure the drawn cord 114 so that the proximal chute 106 is maintained in the closed condition. One skilled in the art would understand that other configurations for transitioning the proximal chute 106 to the closed condition are envisioned. For example, instead of having a series of flexible loops 112, the proximal chute 106 can have one flexible loop, i.e., a continuous flexible tunnel, formed around the outer perimeter 110. The cord 114 can be threaded through the continuous tunnel and used to transition the proximal chute 106 to the closed condition in a similar manner as described above.

Alternatively, or in addition to the above, a user can close the proximal chute 106 by twisting and/or squeezing the proximal chute 106 into the closed condition. For example, the user can transition the proximal chute 106 into the partially closed condition of FIG. 1 and then twist/squeeze the proximal chute 106 so that a prosthesis within the device 100 and/or chamber 124 is completely or substantially prevented from egressing from the device 100 through the opening 122.

Figure 4:
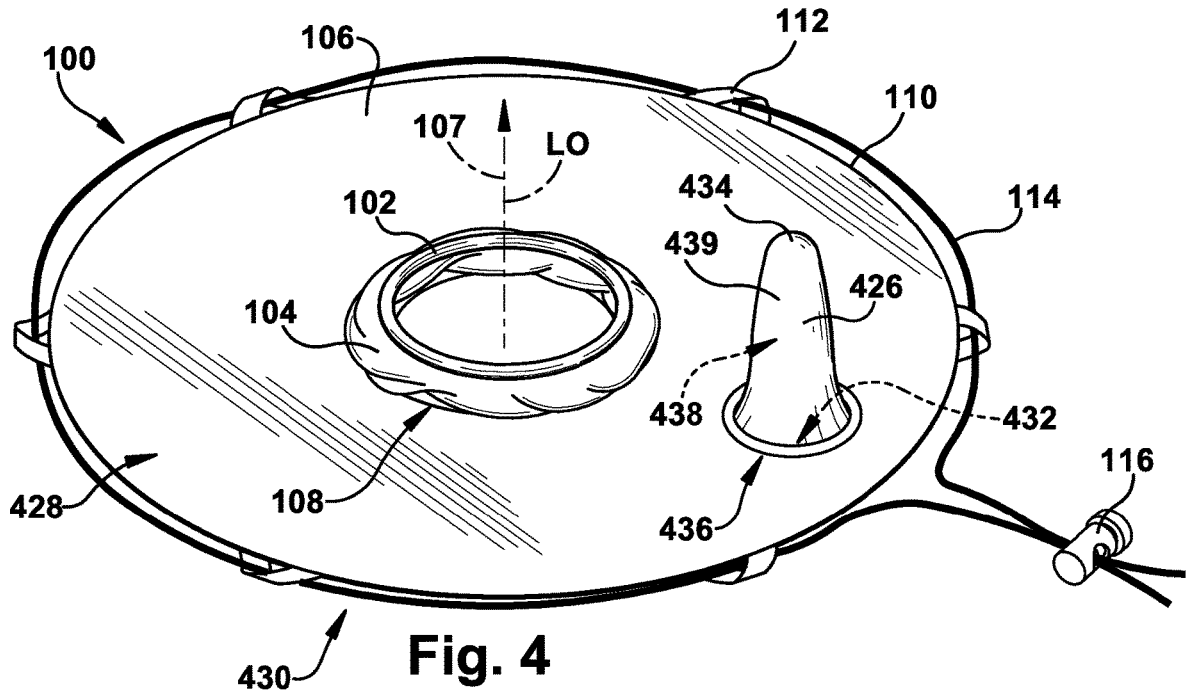
FIG. 4 is a perspective view showing an example device for delivering a prosthesis to a surgical pocket in accordance with an aspect of the present disclosure, including the device in the second condition.

As shown in FIG. 4, the device 100 can include at least one pocket 426 for accessing an interior side 428 of the device 100 from an exterior side 430 of the device 100. In the example configuration shown in FIG. 4, the device 100 has one pocket 426. The pocket 426 has an open end 432 attached to the proximal chute 106 on the interior side 428 of the device 100, and an opposite, closed end 434. The pocket 426 can be attached to the proximal chute 106 by being bonded, sealed, sewn, adhered, by any other suitable direct or indirect attachment or coupling means, or by any combination thereof. Alternatively, the pocket 426 can be attached to the proximal chute 106 by being integrally or monolithically formed as one piece with the proximal chute 106. The open end 432 circumferentially surrounds an aperture 436 in the proximal chute 106 so that a user can access an interior 438 of the pocket 426 through the aperture 436. As shown in FIG. 4, the aperture 436 is positioned radially between the inner and outer perimeters 108, 110 of the proximal chute 106.

The pocket 426 is configured to receive one or more of the user's fingers so that the user can manipulate a prosthesis held in the device 100 or within a surgical skin pocket of a patient while avoiding contact between the prosthesis and any surface/object outside of the device 100 and/or outside of the surgical skin pocket. Additionally, because the pocket 426 is only open at the open end 432, the user cannot directly contact the prosthesis when using the pocket 426 or pass any object completely through the pocket 426 to the interior side 428 of the device 100. Instead, the user can only indirectly contact the prosthesis through one or more wall(s) 439 of the pocket 426 that define the pocket 426. If the user desires to pass an object completely through the proximal chute 106 to the interior side 428 of the device 100, the user can pass the object through the opening 122 of the proximal chute 106.

The distal ring 102 can be comprised of a flexible material. In one instance the distal ring 102 can be made out of an elastic and/or flexible material that allows the distal ring 102 to be compressed to a compressed condition and to self-expand from the compressed condition. The distal ring 102 can be compressed by a user applying a compressive force to the distal ring 102, and can self-expand to a non-compressed condition upon the removal of the compressive force. In the compressed condition, at least one dimension of the distal ring 102 is diminished so that the distal ring 102 can be more easily inserted into a patient than if the distal ring 102 was not compressed. In certain instances, the flexible ring 102 can be at least partially formed from nylon, rubber, latex-free rubber, polyvinyl chloride, silicone, polyethylene, polypropylene, any other flexible material, any other flexible biocompatible material, or any combination thereof. In certain instances, the distal ring 102 can transparent or semi-transparent so a physician can see at least a portion of the prosthesis during use.

The transition tunnel 104 can be comprised of a flexible material. In certain instances the transition tunnel 104 is also comprised of a structured material. For example, the transition tunnel 104 can be comprised of nylon with a structured netting. In certain instances, the netting can be made out of polyvinyl chloride. In certain instances, the transition tunnel 104 can be at least partially formed from nylon, rubber, latex-free rubber, polyvinyl chloride, silicone, polyethylene, polypropylene, any other flexible material, any other flexible biocompatible material, or any combination thereof. In certain instances, the transition tunnel 104 can transparent or semi-transparent so a physician can see at least a portion of the prosthesis during use.

In further instances, the transition tunnel 104 can be semi-expandable and/or flexible to accommodate a prosthesis transitioning from the device 100 into a surgical skin pocket in a controlled manner so that the prosthesis doesn't undesirably and uncontrollably deploy into the surgical skin pocket. Therefore, the user can manipulate the transition tunnel 104 to at least somewhat expand the transition tunnel 104 when desired in order to help pass the prosthesis through the transition tunnel 104 and out from the device 100 into the patient's surgical skin pocket in a controlled manner. Manipulation of the transition tunnel 104 can also cause the prosthesis to elastically deform to a shape and/or size that is configured to pass through and out of the device 100. The transition tunnel 104 can also be semi-rigid in order to resist the compressive effect of a skin tunnel that leads to the surgical skin pocket of a patient, allowing the skin tunnel to be "propped open" by at least the transition tunnel 104. The skin tunnel may be formed from the patient's skin at an incision site, and/or may be a passage or aperture in the flesh of the patient connecting an ambient space to a desired surgical skin pocket.

In addition to being at least semi-expandable, the transition tunnel 104 can also be at least semi-collapsible. In such a configuration, the transition tunnel 104 can at least partially collapsible longitudinally inward on itself to reduce a longitudinal length of the transition tunnel 104. As shown in FIGS. 2 and 4, the device 100 can be substantially flat when the transition tunnel 104 is collapsed and the proximal chute 106 is in the opened condition.

The proximal chute 106 can be comprised of a flexible material. For instance, the proximal chute 106 can be made out of a nylon fabric. In specific instances, the nylon can be a soft nylon fabric. In certain instances, the proximal chute 106 can be at least partially formed from nylon, rubber, latex-free rubber, polyvinyl chloride, silicone, polyethylene, polypropylene, any other flexible material, any other flexible biocompatible material, or any combination thereof. In certain instances, the proximal chute 106 can be transparent or semi-transparent so a physician can see at least a portion of the prosthesis during use. Alternatively, the proximal chute can be opaque. In certain instances, the flexible loops 112 can be made out of the same material as the proximal chute 106 or from a different material.

One skilled in the art would be able to envision a variety of materials that the cord 114 could be made out of. For example, the cord 114 could be made out of Kevlar or nylon.

The pocket 426 can be comprised of a flexible material. For instance, the pocket 426 can be made out of the same materials as the proximal chute 106. In such a configuration, the pocket 426 can be integrally formed as one-piece with the proximal chute 106, or separately formed from and attached to the proximal chute 106. Alternatively, the pocket 426 can be made out of materials different from those used to form the proximal chute 106. In such a configuration, the pocket 426 can be separately formed from and attached to the proximal chute 106. In certain instances, the pocket 426 can be at least partially formed from nylon, rubber, latex-free rubber, polyvinyl chloride, silicone, polyethylene, polypropylene, any other flexible material, any other flexible biocompatible material, or any combination thereof. In certain instances, the pocket 426 can transparent or semi-transparent so a physician can see at least a portion of their finger(s) and/or at least a portion of the prosthesis during use.

Another aspect of the present disclosure is directed to a process 540 for inserting a pre-filled implant into a surgical skin pocket of a subject. As shown in FIG. 5, the process 540 can include step 542 that involves providing a device 100. As described previously, the device 100 can include a distal ring 102, a proximal chute 106, and a transition tunnel 104 that is coupled to the distal ring 102 and the proximal chute 106. At 544, the process 540 can further comprise placing the pre-filled implant into the opened proximal chute 106 of the device 100 and subsequently closing the proximal chute 106. At 546, the pre-filled implant can be manually maneuvered from the proximal chute 106 into the transition tunnel 104 of the device 100. At 548, the distal ring 102 can be placed in the surgical skin pocket. At 550, the distal ring 102 and the transition tunnel 104 of the device 100 can be manually manipulated to insert the pre-filled implant into the surgical skin pocket. In certain instances, when the distal ring 102 is initially inserted into the surgical skin pocket, it can be in a compressed configuration so that the distal ring 102 can be fit into the surgical skin pocket. Upon placement of the distal ring 102 into the surgical skin pocket the distal ring 102 can expand which prevents the distal ring 102 from undesirably being removed from the surgical skin pocket and allows the pre-filled implant to exit the device 100 as desired. When the pocket 426 is present, the user can insert their finger(s) into the interior 438 of the pocket 426. The pre-filled implant can then be oriented as desired in at least one of the device 100 and the surgical skin pocket by the user's finger(s) that are in the pocket 426. The process 540 prevents the pre-filled implant from touching surfaces outside the device 100 and/or outside of the surgical skin pocket. In further instances, the pre-filled implant is a silicone implant.

In certain instances, the distal ring 102 can be placed in the surgical skin pocket prior to placing the pre-filled implant into the proximal chute 106. For example, the distal ring 102, and optionally the transition tunnel 104, can be inserted into the surgical skin pocket. The pre-filled implant can then be placed on the opened proximal chute 106. The proximal chute 106 can be moved to the opened condition prior to or after the distal ring 102 is inserted into the surgical skin pocket. Once the pre-filled implant is on the opened proximal chute 106, the proximal chute 106 can be transitioned to the closed condition to capture the pre-filled implant. Portions of the device 100, such as, for example, the transition tunnel 104 and/or the proximal chute 106, can then be manually manipulated to deliver the pre-filled implant into the surgical skin pocket.

In certain instances, the transition tunnel 104 is hydrated before the pre-filled surgical implant is placed in the proximal chute 106. In other instances, the proximal chute 106 is hydrated before the pre-filled surgical implant is placed in the proximal chute 106. In certain instances, the transition tunnel 104 and the proximal chute 106 are hydrated before the pre-filled surgical implant is placed in the proximal chute 106. In some instances, the transition tunnel 104 and/or the proximal chute 106 are hydrated with saline.

In a further aspect of the present disclosure, a process 652 for delivering a prosthesis into a surgical skin pocket of a subject is provided. As shown in FIG. 6, the process 652 can include step 654 that involves providing a device 100. As described previously, the device 100 can include a distal ring 102, a proximal chute 106, and a transition tunnel 104 that is coupled to the distal ring 102 and the proximal chute 106. At 656, the distal ring 102 of the device 100 can be placed in the surgical skin pocket. In certain instances, when the distal ring 102 is initially inserted into the surgical skin pocket, the distal ring 102 can be in a compressed configuration. Upon placement of the distal ring 102 into the surgical skin pocket the distal ring 102 may be permitted to expand. At 658, the proximal chute 106 can then be spread out into the opened condition so that the proximal chute 106 covers the skin directly surrounding the surgical skin pocket. At 660, an unfilled prosthesis, such as an unfilled breast implant, can be placed into the surgical skin pocket, and at 662, the unfilled prosthesis can be filled. In certain instances, the unfilled prosthesis is filled with saline. When the pocket 426 is present, the user can insert their finger(s) into the interior 438 of the pocket 426. The unfilled prosthesis can then be oriented as desired in at least one of the device 100 and the surgical skin pocket by the user's finger(s) that are in the pocket 426. The process 652 allows, for example, a saline prosthesis to be filled in the surgical skin pocket while preventing, for example, the tubing required to provide the saline as well as the prosthesis, from touching surfaces outside the surgical skin pocket and/or outside of the device 100.

Although the device 100 has been largely described above as delivering filled and unfilled breast implants into a patient, the device 100 may be used for delivering other medical devices, such as, but not limited to, breast implants, calf implants, arm implants, pectoral implants, skull implants, abdominal wall implants, a tissue expander, any other body implants or prosthesis for cosmetic, reconstructive or other purposes, intramedullary nails, hip screws, pacemaker devices, vocal cord paralysis pacers, or any combination thereof, into a patient. For example, the device 100 may be used to deliver a temporary tissue expander into a patient. A temporary tissue expander is a device that may be placed into the patient and then at least partially sealed within the patient. Once placed and sealed, the temporary tissue expander may be expanded slowly over time, while remaining within the patient, to create a desirable surgical skin pocket, create a larger surgical skin pocket than what the temporary tissue expander was inserted into, and/or to stretch the patient's skin. The device 100 may be used to hold open an incision site and/or skin tunnel and help protect the patient's skin from contacting the temporary tissue expander being inserted into the patient.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

I claim:

1. A delivery device configured to deliver a medical device into a surgical skin pocket, the delivery device comprising:

a distal ring;

a transition tunnel sized to receive a medical device, the transition tunnel being coupled to the distal ring; and a proximal chute including an inner perimeter and an outer perimeter, the inner perimeter of the proximal chute being coupled to the transition tunnel, the proximal chute being configured to transition between opened and closed conditions;

at least one flexible loop attached to the outer perimeter of the proximal chute;

a cord extending through the at least one flexible loop, tensioning of the chord causing a size of the opening to reduce and the proximal chute to transition from the opened condition to the closed condition; and a locking device for securing the tensioned cord so that the proximal chute is maintained in the closed condition;

the outer perimeter of the proximal chute in the opened condition being spread radially outward from the transition tunnel and defining an opening for receiving the medical device, the proximal chute in the closed condition being configured to at least partially prevent the medical device from egressing the delivery device.

2. The delivery device of claim 1, wherein when the proximal chute is in the opened condition, the proximal chute is substantially flat.

3. The delivery device of claim 1, wherein when the proximal chute is in the opened condition, the proximal chute is spread into a substantially circular shape.

4. The delivery device of claim 1, wherein when the proximal chute is in the closed condition, the opening defined by the outer perimeter of the proximal chute is at least partially closed to at least partially prevent the medical device from egressing from the delivery device through the opening.

5. The delivery device of claim 1, wherein when the proximal chute is in the closed condition, the proximal chute defines a chamber extending between the transition tunnel and a portion of the proximal chute for capturing the medical device.

6. The delivery device of claim 4, wherein when the proximal chute is in the closed condition, the proximal chute is longitudinally outward from the transition tunnel and the opening is smaller than when the proximal chute is in the opened condition.

7. The delivery device of claim 4, wherein when the proximal chute is in the closed condition, the opening is substantially closed to substantially prevent the medical device from egressing from the delivery device through the opening.

8. A delivery device configured to deliver a medical device into a surgical skin pocket, the delivery device comprising:

a distal ring;

a transition tunnel sized to receive a medical device, the transition tunnel being coupled to the distal ring; and a proximal chute including an inner perimeter and an outer perimeter, the inner perimeter of the proximal chute being coupled to the transition tunnel, the proximal chute being configured to transition between opened and closed conditions, the outer perimeter of the proximal chute in the opened condition being spread radially outward from the transition tunnel and defining an opening for receiving the medical device, the proximal chute in the closed condition being configured to at least partially prevent the medical device from egressing the delivery device; and wherein the proximal chute has an aperture extending therethrough, the delivery device further comprising at least one pocket having an open end attached to the proximal chute and an opposite, closed end, the open end of the pocket circumferentially surrounding the aperture to permit access via the aperture to an interior of the pocket.

9. The delivery device of claim 8, wherein the pocket is only open at the open end.

10. The delivery device of claim 1, wherein the distal ring is configured to be compressed from a non-compressed condition to a compressed condition upon application of a compressive force, the distal ring being self-expandable from the compressed condition to the non-compressed condition upon removal of the compressive force.

11. The delivery device of claim 1, wherein the transition tunnel is comprised of a flexible material.

12. The delivery device of claim 11, wherein the transition tunnel is further comprised of a structured material.

13. The delivery device of claim 1, wherein the transition tunnel is semi-expandable.

14. A process for inserting a pre-filled implant into a surgical skin pocket of a subject comprising:

providing the delivery device of claim 1;

transitioning the proximal chute into the opened condition;

placing the pre-filled implant into the proximal chute of the delivery device through the opening;

with the pre-filled implant in the proximal chute, transitioning the proximal chute to the closed condition;

maneuvering the pre-filled implant from the proximal chute into the transition tunnel;

placing the distal ring in the surgical skin pocket; and manipulating the distal ring and the transition tunnel to insert the pre-filled implant into the surgical skin pocket.

15. The process of claim 14, wherein the proximal chute has an aperture extending therethrough, the delivery device further comprising at least one manipulation pocket having an open end attached to the proximal chute and an opposite, closed end, the open end of the manipulation pocket circumferentially surrounding the aperture so that an interior of the manipulation pocket can be accessed through the aperture, the method further comprising:

orienting the pre-filled implant in at least one of the delivery device and the surgical skin pocket through use of the manipulation pocket.

16. A process for delivering a prosthesis into a surgical skin pocket of a subject comprising:

providing the delivery device of claim 1;

placing the distal ring in the surgical skin pocket;

spreading out the proximal chute into the opened condition so that the proximal chute covers the skin directly surrounding the surgical skin pocket;

placing an unfilled prosthesis into the surgical skin pocket; and filling the prosthesis.

17. The process of claim 16, wherein the proximal chute has an aperture extending therethrough, the delivery device further comprising at least one manipulation pocket having an open end attached to the proximal chute and an opposite, closed end, the open end of the manipulation pocket circumferentially surrounding the aperture so that an interior of the manipulation pocket can be accessed through the aperture, the method further comprising:

orienting the pre-filled implant in the surgical skin pocket through use of the manipulation pocket.

18. The delivery device of claim 1, wherein the medical device is a prosthesis.

\* \* \* \* \*